(12) United States Patent
Sheng et al.

(10) Patent No.: US 10,189,870 B2
(45) Date of Patent: Jan. 29, 2019

(54) CRYSTALLINE FORM OF OXAZOLIDINONE ANTIBIOTICS AND PREPARATION METHOD, COMPOSITION AND USE THEREOF

(71) Applicant: Hangzhou Pushai Pharmaceutical Technology Co., Ltd., Hangzhou, Zhejiang (CN)

(72) Inventors: Xiaoxia Sheng, Zhejiang (CN); Xiaohong Sheng, Zhejiang (CN); Tao Zhu, Zhejiang (CN); Qiang Jia, Zhejiang (CN)

(73) Assignee: HANGZHOU PUSHAI PHARMAEUTICAL TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 15/119,490

(22) PCT Filed: Mar. 27, 2015

(86) PCT No.: PCT/CN2015/075178
§ 371 (c)(1),
(2) Date: Aug. 17, 2016

(87) PCT Pub. No.: WO2015/158202
PCT Pub. Date: Oct. 22, 2015

(65) Prior Publication Data
US 2017/0008919 A1  Jan. 12, 2017

(30) Foreign Application Priority Data
Apr. 18, 2014 (CN) .......................... 2014 1 0158198

(51) Int. Cl.
| | |
|---|---|
| *C07F 9/06* | (2006.01) |
| *C07D 413/14* | (2006.01) |
| *C07F 9/6558* | (2006.01) |
| *A61K 9/20* | (2006.01) |
| *A61K 9/28* | (2006.01) |
| *A61K 31/675* | (2006.01) |
| *A61K 9/48* | (2006.01) |

(52) U.S. Cl.
CPC ........ *C07F 9/65583* (2013.01); *A61K 9/2013* (2013.01); *A61K 9/2018* (2013.01); *A61K 9/2027* (2013.01); *A61K 9/2054* (2013.01); *A61K 9/284* (2013.01); *A61K 9/4866* (2013.01); *A61K 31/675* (2013.01)

(58) Field of Classification Search
CPC ............................... C07D 413/14; C07F 9/06

USPC ............................................... 546/22; 514/89
See application file for complete search history.

(56) References Cited

U.S. PATENT DOCUMENTS 6,627,646 B2 * 9/2003 Bakale ................. C07D 401/12
514/303

FOREIGN PATENT DOCUMENTS

| WO | WO 2005/058886 A1 | 6/2005 |
| WO | WO 2010/091131 A1 | 8/2010 |

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
International Search Report for International Application No. PCT/CN2015/075178, State Intellectual Property Office of the P.R. China, China, dated Jul. 1, 2015, 3 pages.
Written Opinion for International Application No. PCT/CN2015/075178, European State Intellectual Property Office of the P.R. China, China, dated Jun. 20, 2015, 5 pages.

* cited by examiner

*Primary Examiner* — Patricia L Morris
(74) *Attorney, Agent, or Firm* — Sterne, Kessler, Goldstein & Fox PLLC

(57) ABSTRACT

The present invention relates to a novel crystalline form of oxazolidinone antibiotics, which has advantages in the aspects of solubility, hygroscopicity, crystallinity and stability; the present invention also relates to a method for preparing the novel crystalline form, a pharmaceutical composition containing thereof and the use thereof in the preparation of drugs for treating and/or preventing diseases caused by microbial infection.

15 Claims, 5 Drawing Sheets

CRYSTALLINE FORM OF OXAZOLIDINONE ANTIBIOTICS AND PREPARATION METHOD, COMPOSITION AND USE THEREOF

FIELD OF THE INVENTION

The present invention relates to the technical field of crystallization in pharmaceutical chemistry. Specifically, it relates to a crystalline form of an oxazolidinone antibiotic TR-701FA, and preparation methods, compositions and uses thereof.

BACKGROUND

TR-701FA is a new oxazolidinone derivative originally developed by Trius Therapeutics Inc. and has entered Phase III clinical trials, showing excellent antibacterial activity and low toxicity to broad-spectrum bacteria. The chemical name of TR-701FA is (R)-3-(4-(2-(2-methyltetrazol-5-yl)pyridine-5-yl)-3-fluorophenyl)-5-hydroxymethyl oxazolidin-2-onedihydrogenphosphate, and its chemical structural formula is as follows:

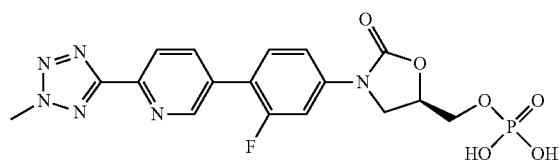 [SMILES: Cn1nnc(-c2ccc(-c3ccc(N4C[C@H](COP(=O)(O)O)OC4=O)cc3F)cn2)n1]

TR-701FA, tedizolid phosphate, is a pro-drug of the active moietytedizolid. Tedizolid is also known as TR-700 or torezolid. Its chemical name is (R)-3-(4-(2-(2-methyltetrazol-5-yl)pyridine-5-yl)-3-fluorophenyl)-5-hydroxymethyloxazolidin-2-one, and its chemical structural formula is as follows:

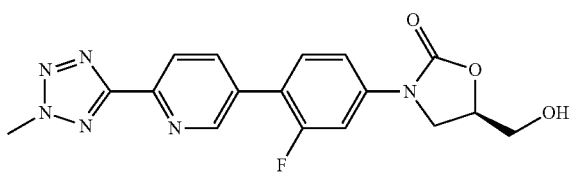 [SMILES: Cn1nnc(-c2ccc(-c3ccc(N4C[C@H](CO)OC4=O)cc3F)cn2)n1]

TR-701FA is activated by plasma esterase and plasma phosphatases in vivo and converts to the active moiety tedizolid, which has anti-bacterial function. TR-701FA has better solubility than tedizolid and it is stable in aqueous solution or acid solution; therefore, it is developed for injective or oral formulations.

Patent document WO2005/058886A1 disclosed Tedizolid and TR-701FA as well as their preparation methods.

Patent document WO2010/091131A1 disclosed a crystalline form of TR-701FA (for convenience, hereinafter referred to as "Form I") and its preparation methods, and characterized the Form I with nuclear magnetic resonance hydrogen spectrum, X-ray powder diffraction pattern, Fourier-Raman spectrum, infrared spectrum, differential scanning calorimetry thermogram and dynamic moisture adsorption diagram.

In the present invention, it was discovered that the Form I of TR-701FA prepared by the method described in the Example 1 of WO2010/091131A1 has defects, such as low crystallinity, low solubility in water and high hygroscopicity. In order to satisfy the strict requirements for crystalline forms of active pharmaceutical ingredients in drug development, it is very important to develop novel crystalline forms of TR-701FA with more advantageous features.

SUMMARY OF THE INVENTION

In view of the defects in the prior art, the purpose of the present invention is to provide novel crystalline forms of TR-701FA, and their preparation methods, pharmaceutical compositions and uses. Compared with the known crystalline form, the novel crystalline forms of the present invention have one or more improved properties, such as better stability; better solubility; faster dissolution; higher crystallinity; lower hygroscopicity; easier for purification and handling; higher chemical purity; lower residual solvents; lower toxicity; better morphology; better processability for formulation, such as better flowability, powder bonding, density and compatibility; improved dosage appearance; improved bioavailability and efficacy; increased shelf life; suitability for new dosage forms, etc.; in particular, it has higher crystallinity and better solubility.

According to the purpose of the present invention, the present invention provides crystalline form II of TR-701FA (for convenience, hereinafter referred to as "Form II"), and it has the following structural formula:

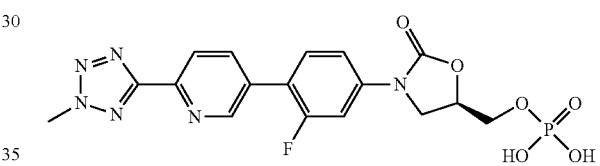

Measured using Cu-Kα radiation, the X-ray powder diffraction pattern of Form II, expressed as 2θ angles, has the following characteristic peaks: 10.5±0.2°, 15.7±0.2°, 16.5±0.2°, 17.3±0.2°, 21.0±0.2° and 26.3±0.2°.

In one preferred embodiment of the present invention, the X-ray powder diffraction pattern of the Form II, expressed as 2θ angles, has the following characteristic peaks: 10.5±0.2°, 12.1±0.2°, 13.9±0.2°, 15.7±0.2°, 16.5±0.2°, 17.3±0.2°, 20.1±0.2°, 21.0±0.2°, 23.9±0.2°, 24.5±0.2°, 26.3±0.2° and 27.6±0.2°.

In one further preferred embodiment of the present invention, the X-ray powder diffraction pattern of Form II, expressed as 2θ angles, has the following characteristic peaks and relative intensities:

| 2θ | Relative intensity (%) |
|---|---|
| 10.5 ± 0.2° | 22.9 |
| 12.1 ± 0.2° | 4.2 |
| 13.9 ± 0.2° | 3.3 |
| 15.7 ± 0.2° | 100.0 |
| 16.5 ± 0.2° | 8.8 |
| 17.3 ± 0.2° | 5.3 |
| 20.1 ± 0.2° | 4.9 |
| 21.0 ± 0.2° | 77.3 |
| 23.9 ± 0.2° | 10.8 |
| 24.5 ± 0.2° | 6.9 |
| 26.3 ± 0.2° | 40.4 |
| 27.6 ± 0.2° | 19.9. |

Non-restrictively, in one embodiment, the X-ray powder diffraction (XRPD) pattern of Form II is shown in FIG. 1.

The polarizing microscope (PLM) picture of Form II shows plate-like crystals.

The thermogravimetric analysis (TGA) thermogram shows that Form II is an anhydrate, with about 0.41% weight loss before 150° C. and a decomposition temperature at about 226° C.

The differential scanning calorimetry (DSC) thermogram shows that Form II has the melting temperature of about 233° C.

The isothermal adsorption curve shows that Form II has the weight variation of about 0.49% within the relative humidity range of 20% to 80% RH.

According to the purpose of the present invention, the present invention provides a preparation method of Form II of TR-701FA, which comprises the following steps: dissolve TR-701FA in a solvent selected from the group consisting of amine, amide and the mixtures thereof, volatilize the solution to dryness, and obtain Form II of TR-701FA.

Preferably, the solvent is selected from the group consisting of N,N-dimethylformamide, N,N-dimethylacetamide, pyridine and the mixtures thereof; and more preferably, N,N-dimethylformamide.

Preferably, the volatilization temperature is from 25° C. to 80° C.; and more preferably, from 60° C. to 80° C.

The operation of "volatilize" or "volatilization" is as follows: a solution in an uncovered reactor is volatilized for crystallization at a corresponding temperature.

In the above preparation method of Form II, the starting material TR-701FA may be the known TR-701FA compound or its crystalline form, including but not limited to, for example, the TR-701FA compound obtained by reference to the preparation method in Example 58 of patent document WO2005058886A1 or Form I of TR-701FA obtained by reference to the preparation method in Example 1 of patent document WO2010091131A1; the starting material TR-701FA may also be in its amorphous form developed by the present invention.

Form II of the present invention has the following beneficial properties and effects:
1) At room temperature, the water solubility of Form II of the present invention and the known Form I is 168 g/mL and 118 μg/mL respectively; therefore, Form II of the present invention has better solubility in water than the known Form I.
2) According to the isothermal adsorption curve, Form II of the present invention has lower hygroscopicity than the known Form I.
3) According to the XRPD pattern and the PLM picture, Form II of the present invention has higher crystallinity.
4) After being stored for 6 months under the conditions of 25° C. and 60% RH, the purity and crystalline form of Form II of the present invention remain unchanged; and after being stored for 10 days under the high-temperature of 80° C. and bright light of 6,000 lx, the decrease of its purity and the increase of its maximum individual impurity content are significantly less than those of the known Form I. Therefore, Form II of the present invention has higher chemical stability and crystalline form stability.

The above advantageous properties of Form II of the present invention show that, compared with the known Form I, Form II of the present invention is more suitable for application in pharmaceutical formulations. It has better powder flowability and better processability it simplifies processes (such as filtration) for drug substances; it improves the content uniformity caused by flowability issues and is beneficial for accurate measurement, efficiency improvement and quality consistency in formulation production. The formulation of Form II of the present invention also has higher dissolution and bioavailability and better antibacterial effect. It is less likely to have content uniformity, stability and formulation processability issues during pharmaceutical production and storage, and thus reduces the risk of efficacy decrease and safety issue caused thereby, and is conducive to transport and store.

The present inventors also developed an amorphous form of TR-701FA (for convenience, hereinafter referred to as "Amorphous Form") and its preparation methods.

Non-restrictively, one typical example of the Amorphous Form has the X-ray powder diffraction (XRPD) pattern as shown in FIG. 9, indicating no characteristic peaks.

The DSC thermogram of the Amorphous Form shows a broad and large exothermic peak from 140 to 190° C. and a melting temperature about 226° C.

The preparation method for the Amorphous Form comprises the following steps: dissolve TR-701FA in a mixed solvent of water and trifluoroethanol, concentrate the obtained solution to dryness under the reduced pressure, and obtain the Amorphous Form.

Preferably, the volume ratio of water to trifluoroethanol in the mixed solvent is from 1:2 to 1:5, and more preferably 1:4.

Preferably, the temperature to concentrate the solution is from 40° C. to 60° C., and more preferably 50° C.

The detailed operation of "concentrate under a reduced pressure" is as follows: place a vessel filled with solution onto a rotary evaporator; in a water bath at a temperature in the range between room temperature and the boiling point of the solvent and under a pressure below the atmosphere (preferably below 0.08 MPa), rotate the evaporator at 10 to 180 rpm (preferably 50 to 100 rpm) to eliminate the solvent.

In the preparation method of the Amorphous Form, the raw material TR-701FA may be the known compound or its crystalline form, including but not limited to, for example, the TR-701FA compound obtained by reference to the preparation method in Example 58 of the patent document WO2005058886A1 or Form I of TR-701FA obtained by reference to the preparation method in Example 1 of the patent document WO2010091131 A1; TR-701FA may also be Form II of TR-701FA developed by the present invention.

In the present invention, "room temperature" refers to 10 to 30° C.

In the present invention, "Form" or "crystalline form" refers to the crystalline form being identified by the X-ray powder diffraction pattern shown herein. It is known to those skilled in this field that the experimental errors depend on conditions of instruments, preparations for samples and purity of samples. The X-ray powder diffraction pattern may change with the change of the instrument conditions: the relative intensities of peaks are likely to change with changes of experimental conditions; therefore, the order of peak intensities should not be regarded as the only or the determining factor; experimental errors of peak angles should be considered and generally the allowed errors are ±0.2°; due to the influence of the experimental factors such as sample height, peak angles may have an overall shifting; generally, certain shifting is allowed. Hence, those skilled in this field may understand that, any crystalline form having characteristic peaks in the X-ray powder diffraction pattern same as or similar to those of the present invention should be within the scope of the present invention. The mentioned "singular crystalline form" refers to the singular crystalline form determined by the X-ray powder diffraction.

Form II of the present invention is pure and singular and substantially free of any other crystalline forms or Amorphous Form. "Substantially free of" in the present invention, when used to refer to a new crystalline form, means that other crystalline forms or Amorphous Form presented in such new crystalline form is less than 20% (weight), further less than 10% (weight), furthermore less than 5% (weight), particularly less than 1% (weight).

The "Anhydrate" mentioned in the present invention refers to a sample with its water content of no more than 1.5% (weight) or 1.0% (weight) measured by TGA.

According to the purpose of the present invention, the present invention provides a pharmaceutical composition, which comprises a therapeutically and/or preventively effective amount of active pharmaceutical ingredient selected from Form II of TR-701FA of the present invention or Form II of TR-701FA prepared by the preparation method of the present invention, and at least one pharmaceutically acceptable carrier or adjuvant. Moreover, the pharmaceutical composition may also comprise other crystalline forms or Amorphous Form of TR-701FA or their pharmaceutical acceptable salts. Optionally, the pharmaceutical composition may also comprise one or more other active pharmaceutical ingredient(s).

The pharmaceutical composition may be solid, semi-solid or liquid and may be prepared in proper dosage forms such as solid dosage forms including tablets, granules, pulvis, pills, powders, capsules; liquid dosage forms including solutions, syrups, suspensions, dispersants and emulsions; injectable dosage forms including solutions, dispersants and solid forms suitable for reconstitution or resuspension before injection, such as lyophilized solids. The formulation may be suitable for immediate-release, sustained-release or controlled-release of the active ingredients. The formulation may be a standard dispersable, chewable, orally dissolving or quickly dissolving formulation. The administration routes include, oral administration, stomach feeding tube administration, duodenum feeding tube administration, intravenous administration, intraarterial administration, intramuscular administration, subcutaneous administration, intraosseous administration, intracutaneous administration, intravaginal administration, rectal administration, intraperitoneal administration, transdermal administration, nasal administration, eye-drop administration, ear-drop administration, etc.

The pharmaceutically acceptable carriers or adjuvants in the above pharmaceutical composition, in the case of solid forms, include but not limited to: diluents, such as starch, modified starch, lactose, powdered cellulose, microcrystalline cellulose, anhydrous calcium hydrogen phosphate, tricalcium phosphate, mannitol, sorbitol and sucrose, etc.; binders, such as Arabic gum, guar gum, gelatin, polyvinylpyrrolidone, hydroxypropyl cellulose, hydroxypropyl methylcellulose, polyethylene glycol, and copovidone, etc.; disintegrating agents, such as starch, carboxymethyl starch sodium, sodium starch glycolate, pregelatinized starch, crospovidone, croscarmellose sodium and colloidal silicon dioxide, etc.; lubricants stearic acid, magnesium stearate, zinc stearate, sodium benzoate and sodium acetate, etc.; glidants, such as colloidal silicon dioxide, etc.; complex-forming agents, such as cyclodextrins and resins of various levels; release rate controlling agents, such as hydroxypropyl cellulose, carboxymethyl cellulose, hydroxypropyl methyl cellulose, ethyl cellulose, methyl cellulose, methyl methacrylate and wax, etc. Other pharmaceutically acceptable carriers and additives include but not limited to film-forming agent, plasticizer, coloring agent, flavoring agent, viscosity regulator, preservative and antioxidant, etc. In the case of oral tablets, the commonly used carriers or adjuvants include lactose, sucrose, sorbitol or mannitol; fibrins, such as corn starch, wheat starch, gelatin, methyl cellulose, hydroxypropyl methyl cellulose, sodium carboxymethyl cellulose and polyvinyl pyrrolidone; lubricants, such as magnesium stearate; disintegrating agents such as crospolyvinylpyrrolidone. Further, tablets may be coated such as sugar coated layer. In the case of oral capsules, the useful carriers or adjuvants include lactose, polyethylene glycol with high or low molecular weight and dried corn starch. In the case of gelatin capsules, the powder carriers include lactose, starch, cellulose derivatives, magnesium stearate, stearic acid and analogues; in the case of soft capsules, the active compound may dissolve or suspend in a proper liquid, such as fat oil, liquid paraffin or liquid polyethylene glycol; in the case of oral suspensions, the active compound can be mixed with the emulsifier and suspending agent. If necessary, some sweeteners and/or flavoring agents and or/or coloring agents can be included in the formulations. Each carrier or adjuvants must be acceptable, be compatible with other ingredients in the formulation and be harmless to patients.

The pharmaceutical composition may be prepared with the method known to those skilled in this field. In preparing of the pharmaceutical composition, Form II of TR-701FA of the present invention is mixed with one or more pharmaceutically acceptable carriers or adjuvants, optionally, with one or more other pharmaceutical active ingredient(s). Solid compositions may be made by direct mixing or granulating processes, while liquid compositions may be made by dissolution or dispersing processes.

Further, the present invention provides use of Form II of TR-701FA of the present invention or Form II of TR-701FA obtained by the preparation method of the present invention in the manufacture of drugs for treating and/or preventing microbial infection diseases.

Further, the present invention provides a method for treating and/or preventing microbial infection diseases, which comprises administrating to patients in need a therapeutically and/or preventively effective amount of Form II of TR-701FA of the present invention or Form II of TR-701FA obtained by the preparation method of the present invention or their pharmaceutical compositions. The patients refer to mammals, such as human. It is obvious to those skilled in this field that the dose administered and the specific administration route will vary depending on such factors as age, weight, diet, seriousness of infection, other medications in uses. The therapeutically effective amount refers to the amount of the compound that can effectively prevent, mitigate or improve disease and symptoms or prolong the survival of the treated objects. For adult patients, the daily oral dose of active ingredients is approximately 0.1 mg to 2,000 mg, preferably, approximately 1 mg to 500 mg; the dose for active ingredients by intravenous administration, intramuscular administration or subcutaneous administration is approximately 0.01 mg to 100 mg and preferably, approximately 0.1 mg to 60 mg.

The aforesaid microbial infections include but not limited to skin infection, pneumonia, infection after virus infection, abdominal infection, urinary tract infection, bacteremia, septicemia, endocarditis, atrioventricular septal infection, vascular puncture infection, meningitis, surgical prophylaxis, peritoneal infection, bone infection, joint infection, methicillin-resistant *staphylococcus aureus* infection, vancomycin-resistant *enterococcus* infection, linezolid-resistant organism infection and tuberculosis.

EXAMPLES

Figure 1:
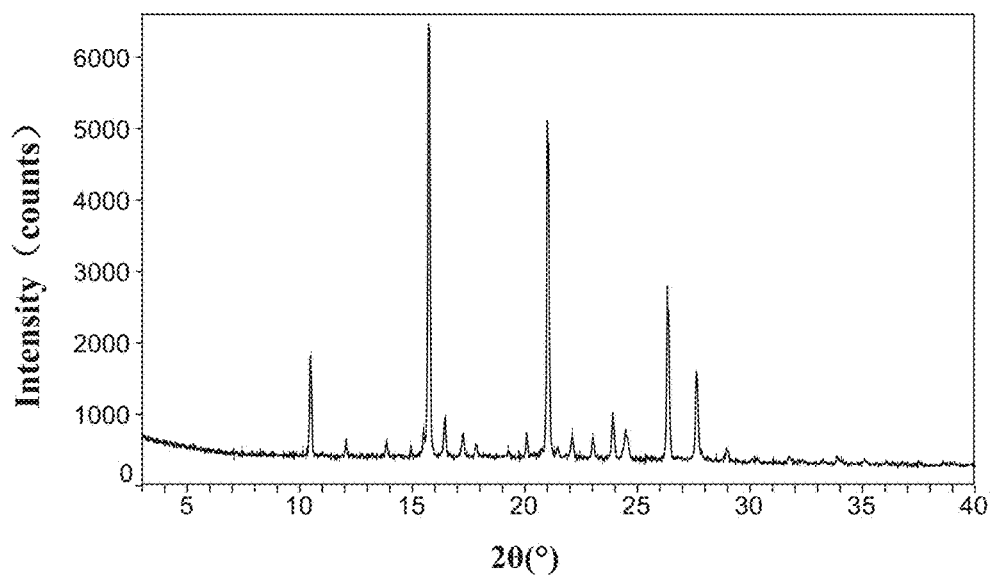
FIG. 1 is the XRPD pattern of Form II of the present invention.

The following examples are helpful to further understand the present invention rather than limit the contents of the present invention.

Instruments and Characterization Methods:

X-ray powder diffraction (XPRD): The instrument is Bruker D8 Advance diffractometer equipped with θ-2θ goniometer, Mo monochromator and Lynxeye detector, which adopts the Cu Kα X-ray with 1.54 nm in wavelength under the operation conditions of 40 kV and 40 mA. Prior to use, the instrument is calibrated with corundum. The collection software is Diffrac Plus XRD Commander. Samples are placed on non-reflective plate to test at room temperature. The detailed testing conditions are as follows: range of angle: 3 to 40°2θ; step size: 0.02*2θ; speed: 0.2 s/step.

Polarized Light Microscope (PLM) pictures are collected from XP-500E polarized light microscope (by Shanghai Changfang Optical Instrument Co., Ltd). Place a small amount of powder sample on a slide glass, drip some mineral oil to disperse the powder sample, cover the sample with a slide glass, then place the sample on the loading table of XP-500E polarized light microscope, choose an appropriate magnitude to observe the morphology of the sample and take pictures.

The Differential Scanning Calorimeter (DSC) data are collected by TA Instruments Q200 MDSC. The instrument control software is Thermal Advantage and the analysis software is Universal Analysis. Generally, take 1 to 10 mg of the sample and place it in an aluminum pan, under the protection of 40 mL/min dry $N_2$, heat the sample from room temperature to 300° C. at the heating rate of 10° C./min.

The thermogravimetric analysis (TGA) data are collected by TA Instruments Q500 TGA. The instrument control software is Thermal Advantage and the analysis software is Universal Analysis. Generally, take 5 to 15 mg of sample and place it in a platinum pan, adopt the segmental high-resolution testing mode, under the protection of dry nitrogen (at 40 mL/min), heat the sample from room temperature to 300° C. at the heating rate of 10° C./min.

The Isothermal Adsorption Curve data are collected by TA Instruments Q5000 TGA. The instrument control software is Thermal Advantage and the analysis software is Universal Analysis. Generally, take 1 to 10 mg of the sample and place it in a platinum pan, and record weight changes of the sample during the course of the relative humidity changing from 0% to 80% then to 0%. Depending on samples, different adsorption and desorption steps may be used.

High Performance Liquid Chromatogram (HPLC) analysis data are collected from Agilent 1260 and the chemical workstation is B.04. The corresponding parameters are as follows: chromatographic column Eclipst XDB-C18, 5 μm, 4.6×250 mm, H-005#, column temperature 25° C., flow rate 0.3 ml/min, mobile phase 13% acetonitrile and 87% water (0.0025M ammonium bicarbonate), wavelength 254 nm, sample size 10 μL and operation duration 20 min.

Unless otherwise specified, the reagents used in the examples were commercially purchased.

Preparation Example 1: TR-701FA

TR-701FA was obtained by reference to the preparation method in Example 58 of patent document WO2005/058886A1 with specific operations as follows:

1) In 10 ml of mixture solvent (tetrahydrofuran:methylenechloride=1:1) was dissolved 1 g of (R)-3-(4-(2-(2-methyltetrazol-5-yl)pyridin-5-yl)-3-fluorophenyl)-5-hydroxymethyl oxazolidin-2-one. The solution was added with 0.6 g of tetrazole and 2.3 g of di-tetrabuthyldiisoprophyl phosphoamidite and stirred for 15 hours at room temperature. The reaction mixture was refrigerated to −78° C., added with 0.7 g of metachloroperbenzoic acid and stirred for 2 hours. After the reaction mixture was stirred for 2 hours, the temperature of the reaction mixture was raised to room temperature. The reaction mixture was then added with ethyl acetate. The organic layer, thus separated, was washed with sodium bisulfate, sodium bicarbonate and brine, dehydrated, filtered and concentrated in vacuum, followed by purification with column chromatography thereby to provide (R)-[3-(4-(2-(2-methyltetrazol-5-yl)pyridin-5-yl)-3-fluorophenyl)-2-oxo-5-oxazolidinyl]methyl phosphoric acid ditetrabuthyl ester (68% yield).

2) In 30 ml of methylenechloride was dissolved the compound (0.6 g) obtained from the Step 1). The solution was added with 15 ml of trifluoroacetic acid and then stirred for 1 hour at room temperature. The reaction mixture was concentrated in vacuum to obtain the residue. The residue was crystallized with ethanol and ethyl ether to obtain mono-[(R)-[3-(4-(2-(2-methyltetrazol-5-yl)pyridin-5-yl)-3-fluorophenyl)-2-oxo-5-oxazolidinyl]methyl]phosphate, i.e., TR-701FA 400 mg (53% yield).

Figure 6:
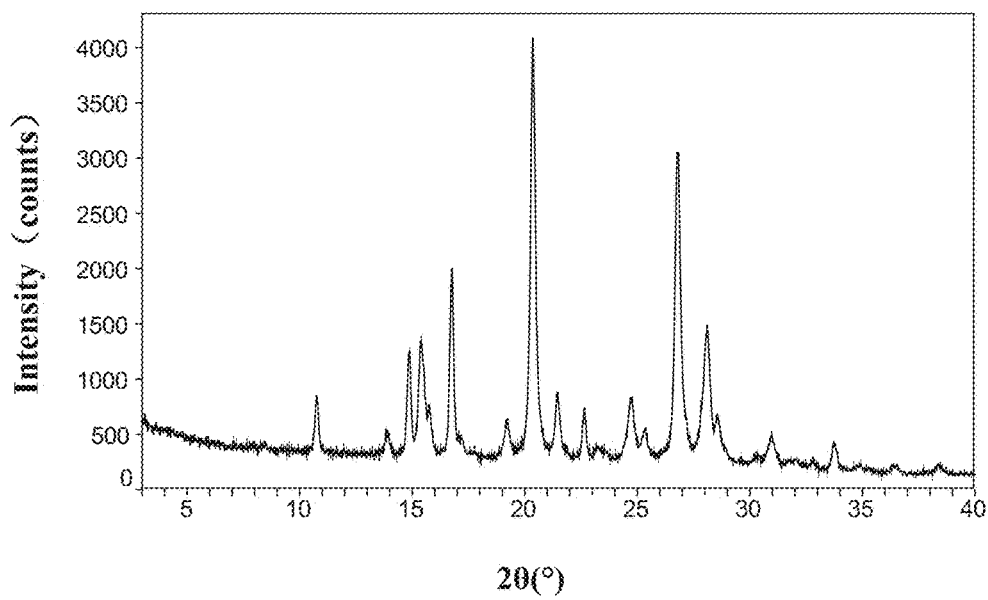
FIG. 6 is the XRPD pattern of the known Form I prepared by reference to WO2005/058886A1.
Figure 7:
FIG. 7 is the PLM picture of the known Form I prepared by reference to WO2005/058886A1.
Figure 8:
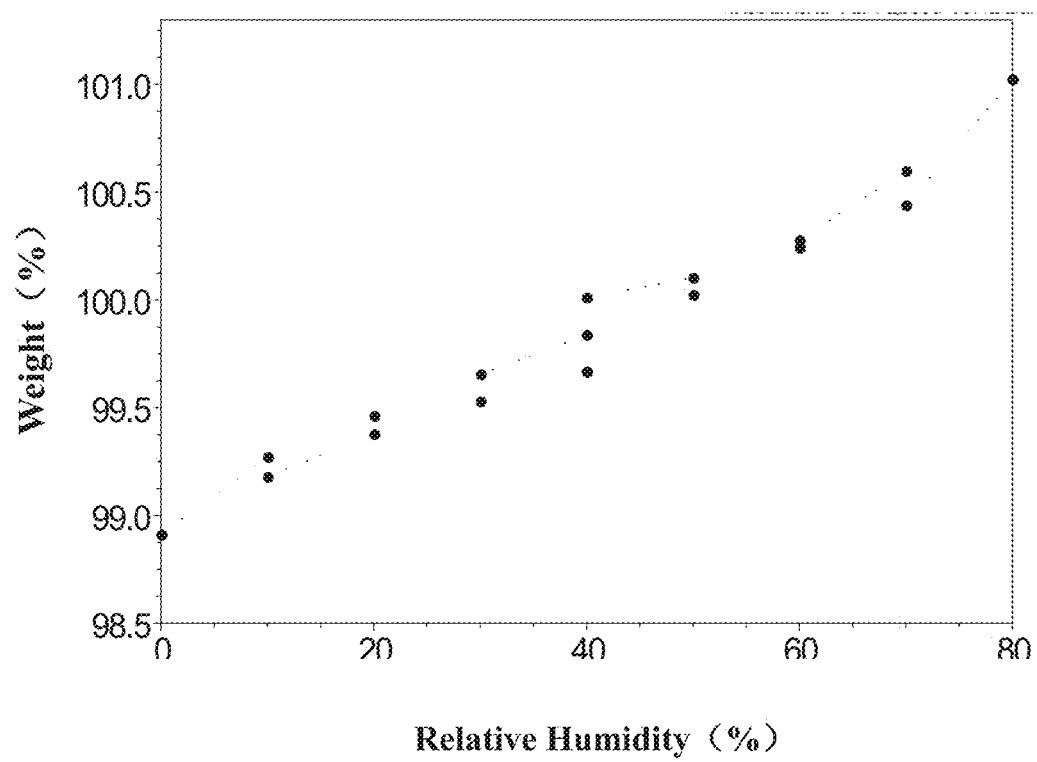
FIG. 8 is the isothermal adsorption curve of the known Form I prepared by reference to WO2005/058886A1.

The further test showed that TR-701FA obtained in the preparation example 1 was the crystals of TR-701FA in the patent document WO2010/091131A1, i.e., Form I of TR-701FA. Its XRPD pattern was shown in FIG. 6 and its PLM picture was shown in FIG. 7, indicating crystalline solids with small particles and low crystallinity; its isothermal adsorption curve was shown in FIG. 8, indicating that its weight change was approximately 1.56% within the relative humidity range of 20% to 80% RH.

Example 1

In 10 mL of N,N-dimethylformamide was dissolved 200 mg of TR-701FA at 80° C. to form a clear solution, the solution was kept at such constant temperature for 10 min, then volatilized to dryness at 80° C., 196 mg of white solid product was obtained with the yield of 98.0%.

The XRPD pattern of the product is shown in FIG. 1, indicating Form II of TR-701FA.

Figure 2:
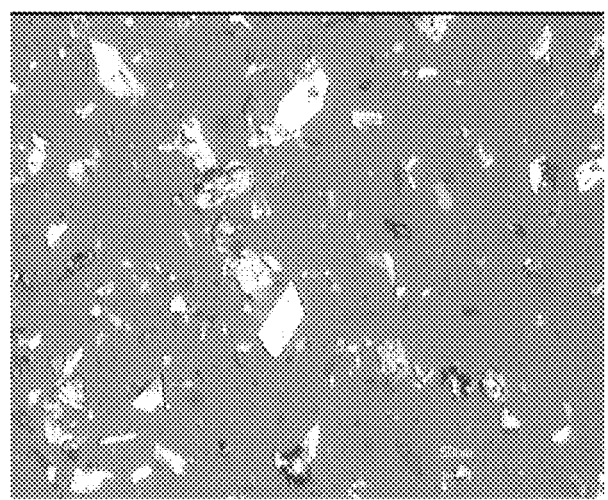
FIG. 2 is the PLM picture of Form II of the present invention.

The PLM picture of the product is shown in FIG. 2, indicating plate-like crystals.

Figure 3:
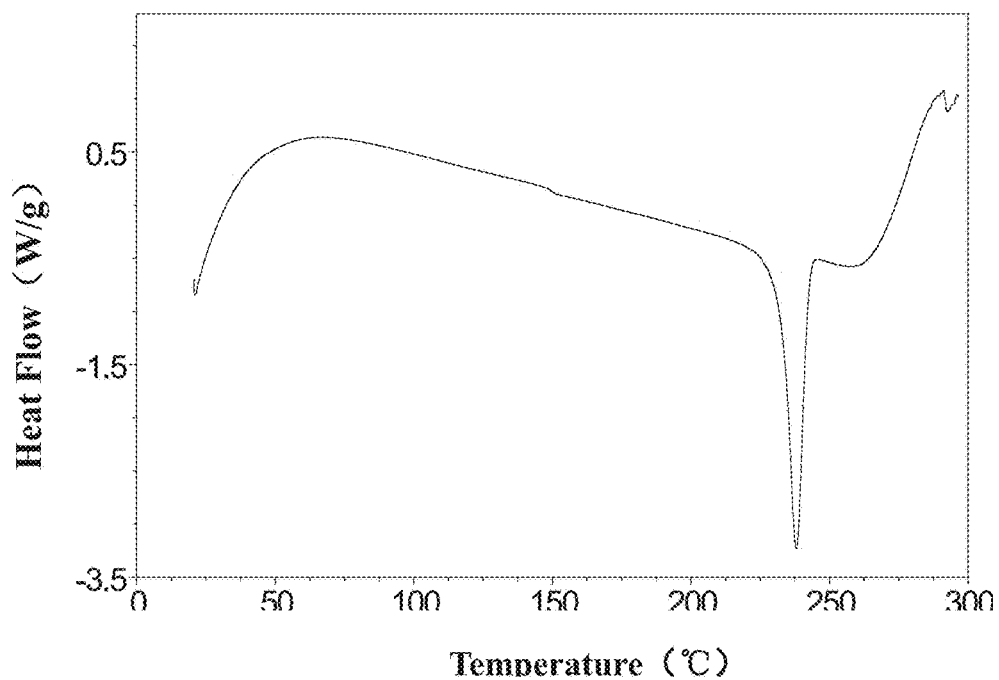
FIG. 3 is the DSC thermogram of Form II of the present invention.

The DSC thermogram of the product is shown in FIG. 3, indicating a melting point of about 233° C.

Figure 4:
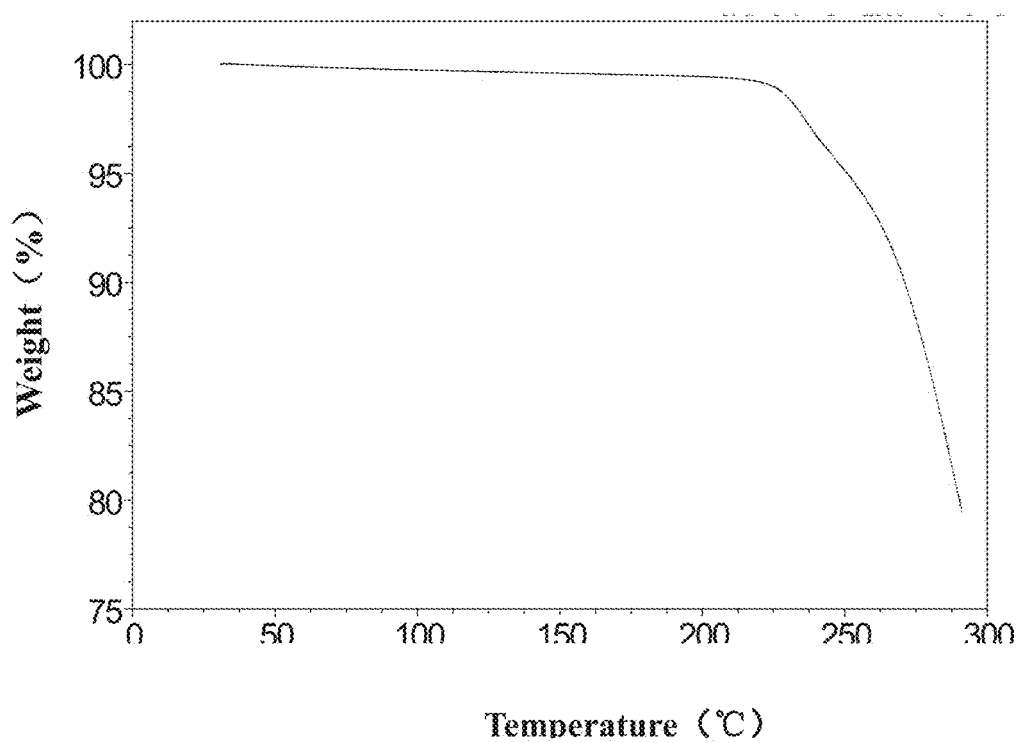
FIG. 4 is the TGA thermogram of Form II of the present invention.

The TGA thermogram of the product is shown in FIG. 4, indicating that the product is anhydrous with a weight loss of about 0.41% before 150° C. and a decomposition temperature of about 226° C.

Figure 5:
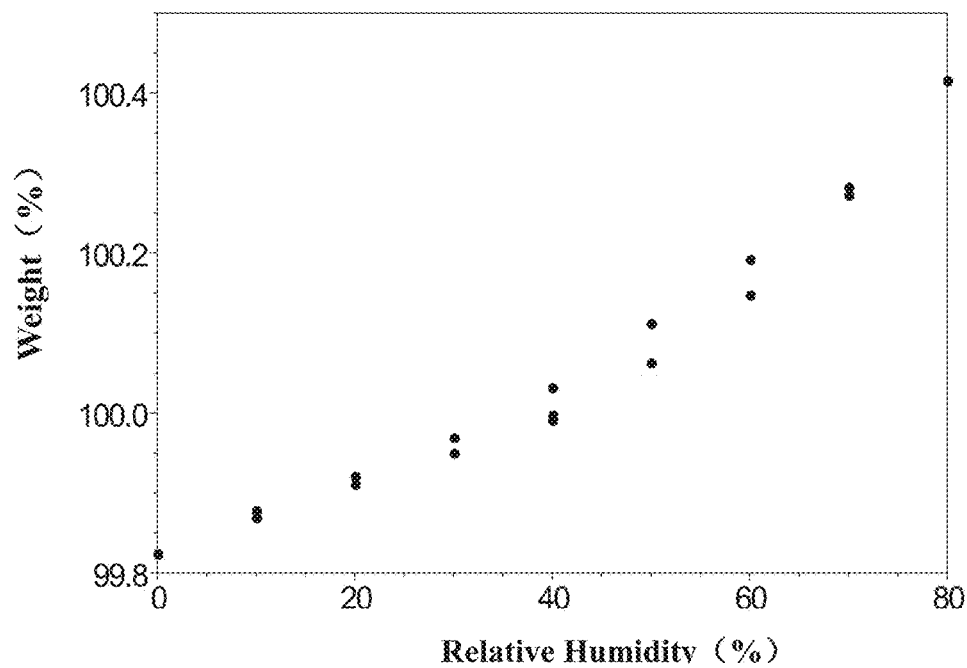
FIG. 5 is the isothermal adsorption curve of Form II of the present invention.

The isothermal adsorption curve of the product is shown in FIG. 5, indicating that a weight change is 0.49% in the relative humidity range of 20% to 80% RH.

Example 2

In 8 mL of N,N-dimethylformamide was dissolved in 100 mg of TR-701FA at 60° C. to form a clear solution. The solution was kept at such temperature for 10 min, then volatilized to dryness at 60° C., 95 mg of Form II of TR-701FA was obtained with the (yield of 95.0%.

Example 3

In 8 mL of pyridine was dissolved 150 mg of TR-701FA at 25° C., filtered, and the filtrate was volatilized to dryness at 25° C., 142 mg of Form II of TR-701FA was obtained with the yield of 94.7%.

XRPD patterns, PLM pictures, DSC thermograms and TGA thermograms (not shown) of the samples prepared in Examples 2 and 3 are the same as or similar to these of the sample prepared in Example 1, indicating that the samples of Examples 2 and 3 have the same crystalline form as the sample obtained in Example 1.

Example 4

In 100 mL mixed solvent of water and trifluoroethanol in the volume ratio of 1:4 was dissolved 100 mg of TR-701FA, filtered, the filtrate was concentrated to dryness by rotating evaporation under a reduced pressure at 40° C., 52 mg of Amorphous Form of TR-701FA was obtained with the yield of 52%.

Figure 9:
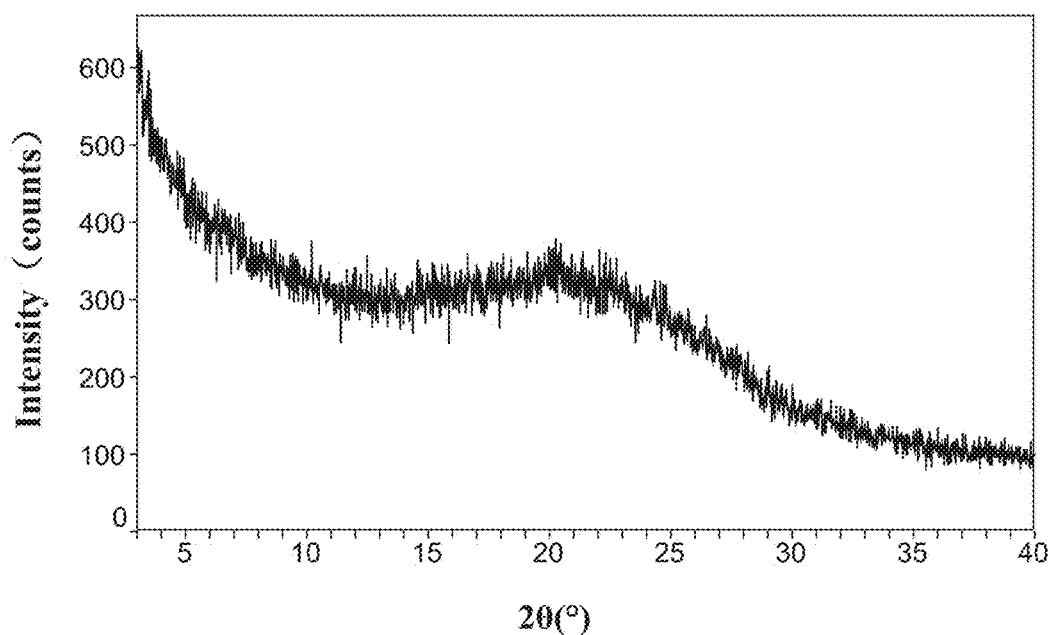
FIG. 9 is the XRPD pattern of the Amorphous Form of the present invention.

The Amorphous Form has the XRPD pattern shown in FIG. 9.

Figure 10:
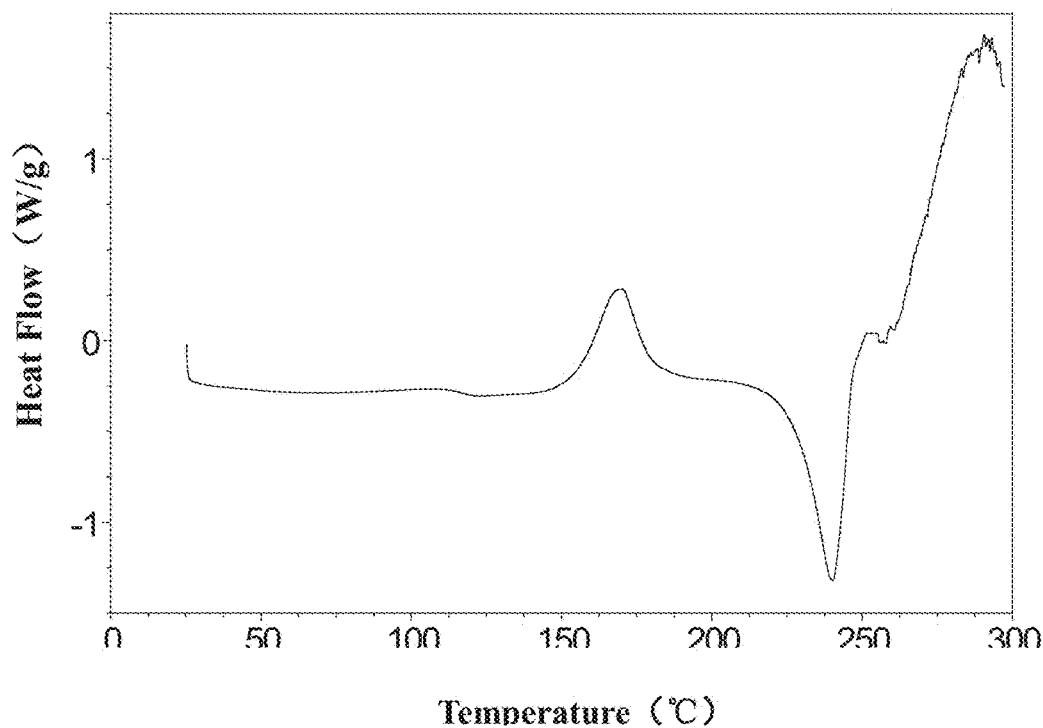
FIG. 10 is the DSC thermogram of the Amorphous Form of the present invention.

The DSC thermogram of the Amorphous Form is shown in FIG. 10, indicating a broad and large exothermic peak at 140-190° C., and fusion melting point of about 226° C.

Example 5

In 100 mL of water was added 20.0 mg of Form I prepared in preparation example 1 or 20 mg of Form II prepared in example 1, and stirred for 10 hours at 25° C., filtered, the content of the filtrate was directly measured by HPLC. The results are as follows: the solubility of Form I was 118 μg/mL and the solubility of Form II was 168 μg/mL.

Example 6

Rapid-release tablets were prepared using Form II of TR-701FA as the active pharmaceutical ingredient and at the strength of 200 mg TR-701FA. Table 1 showed the dosage formula of ingredients in the rapid-release tablet production. Appearing in the final product or not, all ingredients used during the production were listed in Table 1, in which purified water was removed in the production process.

TABLE 1

Formula of Rapid-Release Tablets

|  | Ingredient | Function | Weight (mg/tablet) | Percentage of ingredient to tablet core in weight (%) |
| --- | --- | --- | --- | --- |
| Tablet core | Form II of TR-701FA | Active ingredient | 200.0 | 50.0 |
|  | Microcrystalline cellulose | Diluent | 78.0 | 19.5 |
|  | Mannitol | Diluent | 78.0 | 19.5 |
|  | Povidone | Binder | 16.0 | 4.0 |
|  | crospovidone | Disintegrating agent | 24.0 | 6.0 |
|  | Purified water | Granulating medium | — | — |
|  | Magnesium stearate | Lubricant | 4.0 | 1.0 |
| Coat | Opadry II yellow | Coloring coating | 14.0 | 3.4 |
|  | Purified water | Film coating medium | — | — |
|  | Total weight of tablet |  | 414.0 |  |

Preparation Steps:
1. Sieve and mix Form II of TR-701FA, mannitol, microcrystalline cellulose and crospovidone.
2. Dissolve povidone in purified water to obtain a binder solution.
3. Add the binder solution obtained in Step 2 into the mixture obtained in Step 1, wet granulate and then dry the granules.
4. Mix the sieved magnesium stearate with the dried granules obtained in Step 3, then compress the mixture into tablet cores in a rotary tableting machine.
5. Continuously coat the tablet core obtained in Step 4 with Opadry II yellow aqueous coating solution until 3.4% target weight is reached.

Example 7

Capsules were prepared using Form II of TR-701FA of the present invention as the active pharmaceutical ingredients and at the strength of 182 mg TR-701FA. Table 2 showed the dosage formula of ingredients in the capsule production.

Appearing in the final product or not, all ingredients used in the production were listed in Table 2, in which purified water was removed in the production process.

TABLE 2

Formula of Capsules

| Ingredient | Function | Weight (mg/capsule) | Weight percentage (%) |
|---|---|---|---|
| Form II of TR-701FA | Active ingredient | 182 | 60.7 |
| Microcrystalline cellulose | Diluent | 78 | 26.0 |
| Povidone | Binder | 15.0 | 5.0 |
| crospovidone | Disintegrating agent | 22.0 | 7.3 |
| Purified water | Granulating medium | — | — |
| Magnesium stearate | Lubricant | 3.0 | 1.0 |
| Total weight of capsule fillings | | 300.0 | 100.0 |

Preparation Steps:
1. Sieve and mix Form II of TR-701FA, microcrystalline cellulose and crospovidone.
2. Dissolve crospovidone into purified water to obtain a binder solution.
3. Add the binder solution obtained in Step 2 into the mixture obtained in Step 1, wet granulate and then dry the granules.
4. Mix the sieved magnesium stearate with the dried granules obtained in Step 3, and then fill the mixture into capsules with a capsule filling machine.

Comparative Example 1

Form I of TR-701FA prepared in preparation example 1 and Form II of TR-701FA of the present invention were compared in the stability test by being stored for 10 days under conditions of high temperature and bright light. The high temperature was 80° C. and the light was 6,000 lx. HPLC purities and maximum individual impurity contents of the compounds were tested before and after the storage, and the results were shown in Table 3.

TABLE 3

Results of Stability Test

| Compound | 0 day | | Under conditions of high temperature and lighting for 10 days | | Change in value | |
|---|---|---|---|---|---|---|
| | HPLC purity (%) | Maximum individual impurity content (%) | HPLC purity (%) | Maximum individual impurity content (%) | HPLC purity (%) | Maximum individual impurity content (%) |
| Form I of TR-701FA | 98.7 | 1.3 | 96.6 | 2.5 | 2.1 | 1.2 |
| Form II of TR-701FA | 98.3 | 1.6 | 98.4 | 1.7 | −0.1 | 0.1 |

According to the data in Table 3, under conditions of high temperature and bright light for 10 days, the purity of Form I of TR-701FA decreased by 2.1% and the maximum individual impurity content thereof increased by 1.2%; while the purity of Form II of TR-701FA of the present invention almost unchanged and the maximum individual impurity content thereof only increased by 0.1%. Therefore, the stability of Form II of TR-701FA of the present invention is remarkably better than that of Form I of TR-701FA under conditions of high temperature and bright light.

All patent documents and non-patent documents cited in this specification are incorporated herein by reference in its entirety.

The described above are only specific embodiments of the present invention, but not limitations to the scope of the present invention. Any changes or replacements within the technical scope disclosed by the present invention, made by those skilled in this field without creative labor, shall be fallen within the scope of the present invention.

What is claimed is:

1. Form II of (R)-3-(4-(2-(2-methyltetrazol-5-yl)pyridine-5-yl)-3-fluorophenyl)-5-hydroxymethyl oxazolidin-2-one dihydrogen phosphate represented by the following structural formula:

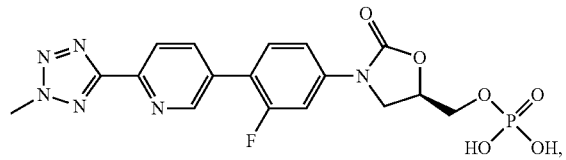 [SMILES: Cn1nnc(-c2ccc(-c3ccc(N4C[C@H](COP(=O)(O)O)OC4=O)cc3F)cn2)n1]

measured with Cu—Kα radiation, the X-ray powder diffraction pattern of the Form II, expressed as 2θ angles, has the following characteristic peaks: 10.5±0.2°, 15.7±0.2°, 16.5±0.2°, 17.3±0.2°, 21.0±0.2° and 26.3±0.2°.

2. Form II of (R)-3-(4-(2-(2-methyltetrazol-5-yl)pyridine-5-yl)-3-fluorophenyl)-5-hydroxymethyl oxazolidin-2-one dihydrogen phosphate according to claim 1, wherein the X-ray powder diffraction pattern, expressed as 2θ angles, has the following characteristic peaks: 10.5±0.2°, 12.1±0.2°, 13.9±0.2°, 15.7±0.2°, 16.5±0.2°, 17.3±0.2°, 20.1±0.2°, 21.0±0.2°, 23.9±0.2°, 24.5±0.2°, 26.3±0.2° and 27.6±0.2°.

3. Form II of (R)-3-(4-(2-(2-methyltetrazol-5-yl)pyridine-5-yl)-3-fluorophenyl)-5-hydroxymethyl oxazolidin-2-one dihydrogen phosphate according to claim 2, wherein the X-ray powder diffraction pattern, expressed as 2θ angles, has the following characteristic peaks and relative intensities:

| 2θ | Relative intensity (%) |
|---|---|
| 10.5 ± 0.2° | 22.9 |
| 12.1 ± 0.2° | 4.2 |
| 13.9 ± 0.2° | 3.3 |
| 15.7 ± 0.2° | 100.0 |
| 16.5 ± 0.2° | 8.8 |
| 17.3 ± 0.2° | 5.3 |
| 20.1 ± 0.2° | 4.9 |
| 21.0 ± 0.2° | 77.3 |
| 23.9 ± 0.2° | 10.8 |
| 24.5 ± 0.2° | 6.9 |
| 26.3 ± 0.2° | 40.4 |
| 27.6 ± 0.2° | 19.9. |

4. A pharmaceutical composition comprising Form II of (R)-3-(4-(2-(2-methyltetrazol-5-yl)pyridine-5-yl)-3-fluorophenyl)-5-hydroxymethyloxazolidin-2-one dihydrogen phosphate according to claim 1, and at least one pharmaceutically acceptable carrier or additive.

5. The pharmaceutical composition according to claim 4, wherein the pharmaceutical composition is a dosage form selected from the group consisting of injectable, tablet and capsule.

6. A pharmaceutical composition comprising Form II of (R)-3-(4-(2-(2-methyltetrazol-5-yl)pyridine-5-yl)-3-fluorophenyl)-5-hydroxymethyl oxazolidin-2-one dihydrogen phosphate according to claim 2, and at least one pharmaceutically acceptable carrier or additive.

7. The pharmaceutical composition according to claim 6, wherein the pharmaceutical composition is a dosage form selected from the group consisting of injectable, tablet and capsule.

8. The pharmaceutical composition according to claim 5, wherein the dosage form is a tablet.

9. The pharmaceutical composition according to claim 7, wherein the dosage form is a tablet.

10. The pharmaceutical composition according to claim 5, wherein the dosage form is a capsule.

11. The pharmaceutical composition according to claim 7, wherein the dosage form is a capsule.

12. A pharmaceutical composition comprising Form II of (R)-3-(4-(2-(2-methyltetrazol-5-yl)pyridine-5-yl)-3-fluorophenyl)-5-hydroxymethyloxazolidin-2-one dihydrogen phosphate according to claim 3, and at least one pharmaceutically acceptable carrier or additive.

13. The pharmaceutical composition according to claim 12, wherein the pharmaceutical composition is a dosage form selected from the group consisting of injectable, tablet and capsule.

14. The pharmaceutical composition according to claim 13, wherein the dosage form is a tablet.

15. The pharmaceutical composition according to claim 13, wherein the dosage form is a capsule.

* * * * *